Figure 1:
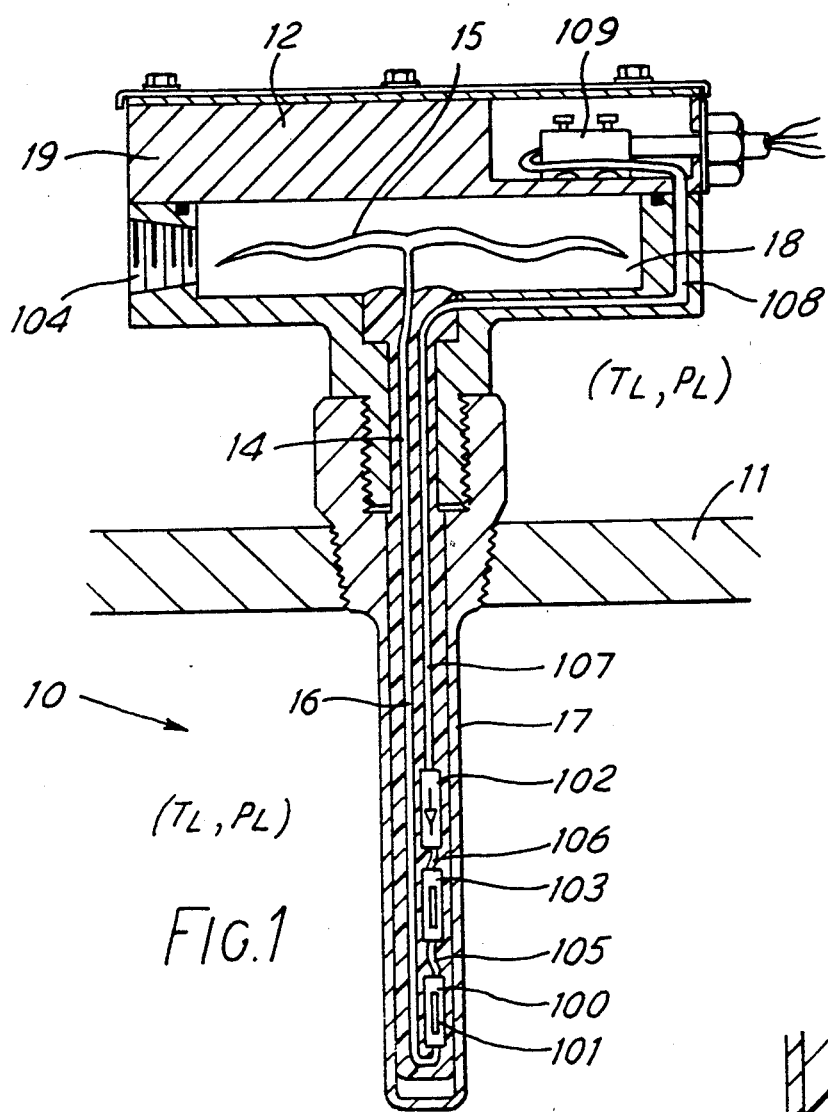

United States Patent [19]

Stansfeld et al.

[11] Patent Number: 5,048,323
[45] Date of Patent: Sep. 17, 1991

[54] FLUID METERING

[75] Inventors: James W. Stansfeld, Hampshire; David I. H. Atkinson, Surrey, both of England

[73] Assignee: Schlumberger Indusrtries Limited, Farnborough, England

[21] Appl. No.: 231,313

[22] Filed: Aug. 11, 1988

[30] Foreign Application Priority Data

Aug. 12, 1987 [GB] United Kingdom ............... 8719105

[51] Int. Cl.$^5$ .............................................. G01N 9/24
[52] U.S. Cl. ................................... 73/32 A; 73/861.02
[58] Field of Search ........................... 73/32 A, 861.02

[56] References Cited

U.S. PATENT DOCUMENTS 4,297,872 11/1981 Ikeda et al. ........................ 73/32 A
4,526,480 7/1985 Ward ................................... 73/32 A

FOREIGN PATENT DOCUMENTS 0101669 2/1984 European Pat. Off. .
2456751 8/1976 Fed. Rep. of Germany .
2633859 2/1978 Fed. Rep. of Germany .
1065280 4/1967 United Kingdom .
1178587 1/1970 United Kingdom .
2009931 6/1979 United Kingdom .
2034895 6/1980 United Kingdom .
2093998 9/1982 United Kingdom .

Primary Examiner—Hezron E. Williams
Assistant Examiner—Rose M. Finley
Attorney, Agent, or Firm—Sanford J. Asman

[57] ABSTRACT

A gas flow correction sensor for producing an output signal proportional to the ratio between line pressure and line temperature for gas flowing in a line, for use in correcting the output of a volumetric flow meter connected in the line, comprises a sealed chamber containing a fixed mass of a reference gas. The sealed chamber includes a bellows portion subjected to line pressure, thus maintaining the reference gas at line pressure. Additionally, the sealed chamber is thermally insulated and includes at least a portion disposed in a thermowell immersed in the line, so as to maintain the reference gas at line temperature. A vibrating quartz density sensor is also mounted in the thermowell, so as to produce an output signal whose frequency is proportional to the density of the reference gas, which can be shown also to be proportional to the desired line pressure to line temperature ratio.

7 Claims, 1 Drawing Sheet

FLUID METERING

This invention relates to fluid metering, and in particular to the correction of metered values so that they may be referred to standard conditions, and to a sensor for this purpose.

The need for correction arises where operational metering conditions are subject to change.

Most gas meters, for example, measure the flow of gas in units of line volume. However for the actual quantity of gas delivered to be assessed, it is desirable that the measurement be referred to standard conditions of temperature and pressure. With some meters, a fixed factor correction is applied, but where accuracy is particularly important, as in fiscal applications, account must be taken that the correction required is, in fact, a function of line temperature and pressure. Thus to refer line volume to standard conditions:

$$V_S = V_L \times \frac{P_L}{P_S} \times \frac{T_S}{T_L} \times \frac{Z_S}{Z_S}$$

Where
 V = Volume
 P = Pressure (absolute)
 T = Temperature (absolute)
 Z = Compressibility factor
 suffix L = denotes at line conditions
 suffix S = denotes at standard conditions Grouping the constant terms together, (assuming that the compressibility of the metered gas is known), as a constant K, the correction required is:

$$V_S = V_L \cdot K \frac{P_L}{T_L}$$

Thus, both line pressure and temperature must be known before correction can be made.

Heretofore, separate measurements of pressure and temperature have been made and used for the purpose of correction. Where a meter providing a corrected output is required, the correction has been applied automatically, but at the cost of providing corrector electronics linked to separate pressure and temperature sensors for deriving the required function and for applying it to the meter output.

It is an object of the present invention to provide a single sensor for gas metering providing the correction function directly.

According to the present invention a gas flow correction sensor for sensing a pressure-temperature function of gas flowing in a line for use in correcting the output of a volumetric flow meter connected in the line comprises:
 a sealed gas-containing chamber;
 means for maintaining the contained gas at line temperature and pressure; and
 a vibrating element density sensing means for producing an output signal whose frequency is dependent upon the density of the contained gas.

It can be shown that the output signal S(t) of a sensor in accordance with the present invention varies in accordance with the function:

$$S(t) = k \cdot \frac{P_L}{T_L}$$

where k is a constant. Hence a direct output of the required correction function is provided.

Preferably, the density sensing means comprises a resonant quartz density sensor, such as a quartz tuning fork sensor, having a resonant frequency proportional to surrounding gas density. Such a sensor may be compensated by a second sensor, subjected only to line temperature, for the purpose of cancelling intrinsic temperature-dependent errors.

Advantageously, the sealed chamber is maintained at line pressure by allowing line pressure to act upon a compressible portion of the chamber, preferably in the form of a bellows.

To further advantage, the sealed chamber is maintained at line temperature by mounting at least a portion thereof in a thermowell entering the line. Any portions external to the line may be thermally insulated from ambient conditions.

Preferably the fluid contained in the sealed chamber is inert, for example gaseous nitrogen or argon. The fluid may be chosen in accordance with sensitivity requirements, since sensitivity is dependent upon gas molecule weight. Advantageously the fluid is chosen to be of comparable compressibility with the fluid being metered.

Preferably the sealed chamber comprises a bellows portion and a capillary tube portion connecting with a small sub-chamber housing the density sensor, the capillary and sub-chamber portions being formed within an elongate probe, adapted to enter the line, for preference through a standard temperature tap, and extending to an externally mounted bellows portion. Preferably the bellows portion is insulated from ambient conditions and adapted to receive a line pressure input from an adjacent line pressure tap. The elongate probe advantageously comprises a thermowell arranged to maintain the sealed chamber at line temperature.

Alternatively, the entire chamber may be adapted to enter the line, with the bellows portion exposed, to be acted on directly by the gas in the line. In any event, it is desirable for the bellows volume to be large compared with the volume of any capillary or sub-chamber portions.

Figure 2:
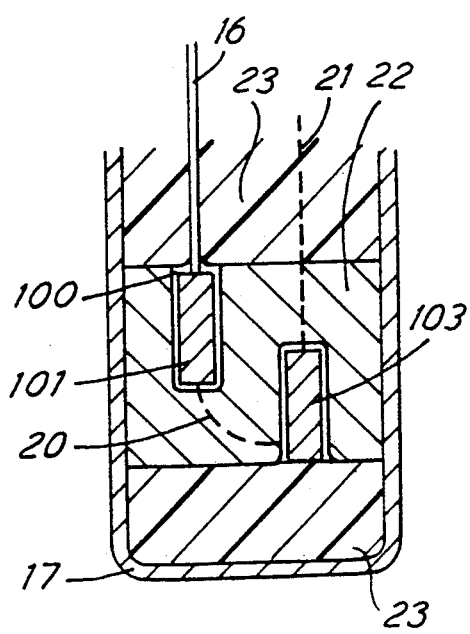

In order that further features and advantages of the present invention may be appreciated an embodiment will now be described, by way of example only, and with reference to the accompanying diagrammatic drawings, of which:

FIG. 1 shows a sensor in accordance with the present invention for the correction of metered values; and FIG. 2 shows part of a probe portion of an alternative embodiment of the sensor of FIG. 1.

The volume of gas flowing through a line 10 (FIG. 1), part of one wall 11 of which is shown, is to be metered, by means not shown, and referred to standard temperature and pressure conditions ($T_S, P_S$) from the prevailing line conditions ($T_L, P_L$). To perform this correction, a signal varying in accordance with a correction function is required and to this end a sensor 12 in accordance with the present invention is arranged to sense line conditions.

The sensor 12 has a sealed gas-containing chamber 14 having a bellows portion 15, in the form of a collapsible structure, sometimes referred to as a diaphragm, and a capillary portion 16, which extends within a probe portion 17 of sensor 12. Bellows 15 lies within an external chamber 18 formed within a thermally insulating casing 19. Probe portion 17 is bonded to casing 19 and adapted to be installed to enter the line 10. Capillary portion 16 extends within the probe portion 17 to a sub-chamber 100 within which is mounted a density sensor 101. Bellows portion 15, capillary portion 16 and sub-chamber 100 are sealed and contain an inert gas.

The density sensor 101 is a vibratory element, formed in quartz for example in a tuning fork configuration. Various types of quartz sensors are known for the measurement of pressure and temperature, in which a quartz crystal is cut and configured to be sensitive to changes in a wanted parameter e.g. pressure, and insensitive to an unwanted parameter e.g. temperature: in the present case, the quartz is cut to be sensitive to changes in density. In the known pressure and temperature sensors, the quartz is normally made to resonate by feedback via a maintaining amplifier to and from piezo-electric transducers formed in the quartz, and the resonant frequency is a function of pressure and a sensor output is provided as a varying frequency signal. A similar arrangement is employed in the present embodiment, and to this end probe portion 17 houses a maintaining amplifier 102 mounted close to the vibratory element for the prevention of excessive electrical pick-up and the avoidance of stray capacitive loading.

Although cut and configured for a minimum response to temperature, the quartz element of the sensor 101 may still exhibit an unacceptable temperature characteristic. In quartz element pressure sensors a reference crystal, not subjected to the pressure to be measured, may be employed to apply a correction. A similar arrangement is employed with the density sensitive element of the present invention, and to this end a reference crystal 103 is mounted within probe portion 17 of the sensor 12, and excited similarly to the sensor 101 by means of another maintaining amplifier (not shown) associated with the maintaining amplifier 102.

Chamber 18 within casing 19 is provided with an orifice 104 to which, in use, a connector (not shown) relays gas at line pressure, so that bellows portion 15 is subjected to line pressure $P_L$. The connector may take any convenient form and for example run as a pipe from an adjacent line pressure tap. Thus the gas in the sealed space defined within bellows 15, capillary portion 16 and sub-chamber 100 is itself at line pressure, $P_L$. For a sensitive sensor, the displaceable volume of bellows 15 is relatively large compared with the volume of the capillary 16 and sub-chamber 100.

Probe portion 17 constitutes a thermowell arranged such that the gas in the sealed chamber is at substantially line temperature $T_L$. Capillary 16, chamber 100, reference sensor 103 and maintaining amplifier 102 are potted into the interior of probe portion 17 by use of a compound of suitable thermal conductivity. This serves not only to maintain the chamber 14 at line temperature, but also gives protection to the components, including the electrical connections 105, 106 intermediate the density sensor 101, reference sensor 103 and maintaining amplifier 102 (and its associated maintaining amplifier for sensor 103), and electrical connection 107 leading via conduit 108 to external connector 109.

In order that features and advantages of the present invention may be yet further appreciated, the theory of operation of the embodiment described above will now be considered.

Generally the resonant frequency of a vibratory quartz element is proportional to the density of the fluid by which it is surrounded and is also a function of temperature. Both of these characteristics have been successfully exploited to provide temperature and pressure sensors based on such elements. In prior art systems, where a vibratory element is mounted for example in a free gas, dependence upon density is problematic since the density of fluid surrounding the sensor is itself dependent upon both temperature and pressure and therefore a density sensitive element cannot by itself be used to sense either pressure or temperature. The solution adopted in the prior art is to use two elements, one to compensate the other in respect of the unwanted parameter. For example a prior art pressure transducer includes two vibratory elements, one subjected to the pressure to be measured and one to a fixed pressure, both being maintained at the same temperature to provide compensation. Similarly, a prior art temperature sensor would include two elements, one subject to the changing temperature to be measured and one to a fixed reference temperature, the pair being subjected to the same pressure. Such an arrangement is described, for example, in European Patent Application 0 101 669A.

By contrast, with the present invention only a single density sensitive vibratory element is required. It is to be noted that the element (for example element 101 of FIG. 1) is contained in a chamber (16) in which there is a fixed mass of fluid.

The output frequency, f, of a vibratory element is proportional to the density, d, of a surrounding gas, i.e. f is proportional to d. It is known that density is mass (m) per unit volume (V), i.e. d=m/V.

Since in the present embodiment a fixed mass of gas is being considered, m is constant, so that:

$$d \text{ is proportional to } \frac{1}{V}$$

By virtue of the ideal gas law, PV=RT, we can write $$V = \frac{RT}{P}, \text{ so that:}$$

$$d \text{ is proportional to } \frac{P}{RT}$$

Since R is a constant for the enclosed gas in question and introducing a constant of proportionality in substituting f for d, $$f = c \cdot \frac{P}{T}$$

Hence it can be clearly seen that the resonant frequency of the vibratory element 101 varies in accordance with the required function P/T, and that in the arrangement described, P and T represent line conditions $P_L$ and $T_L$. The embodiment provides an output whose frequency is directly proportional to the required correction $P_L/T_L$. Such an output is particularly advantageous since it is essentially digital in nature, being easily counted or accumulated in unit time.

In the embodiment described above, vibratory element 101 will exhibit a small temperature dependence of its own. To compensate for this the second crystal 103 maintained at the same temperature and in a fluid of constant density (conveniently a vacuum) is included. This second crystal, which is formed from the same crystal growth and similarly cut, exhibits a substantially identical temperature dependence to measurement crystal 101 and may therefore be used for the cancellation of errors, for example by subtraction of a frequency count accumulated in a unit time interval from the measurement element count over the same time interval.

It will be noted that this latter temperature compensation, described as applied to an embodiment of the present invention for the purpose of correction of the temperature dependence of a vibratory element, is entirely different from the temperature compensation applied to prior art pressure sensors, which exhibit dependence not only by virtue of crystal dependence but also by virtue of being in free fluid conditions. Removal of compensation from such a sensor would completely invalidate results, whereas removal of temperature compensation from the embodiment described herein would merely introduce a small element-dependent temperature error.

In an alternative embodiment (FIG. 2, which shows a part of the probe portion and in which reference numerals common with those of FIG. 1 have been used for the same or similar parts) elements 101 and 103 are mounted in an insert 22 of a material of high thermal conductivity, such as copper, to which capillary tube 16 may be attached to form chamber 100, the whole being made as a sub-assembly and inserted within the inner surface of thermowell 17, with which it is an interference fit. Once assembled and electrical connection 21 made with the maintaining amplifier (not shown), potting compound 23 may be applied.

Electrical connection 20 between elements 101 and 103 and connection 21 between element 103 and the maintaining amplifier may be routed in any convenient way (connections 20 and 21 being shown diagrammatically in FIG. 2), for example by conduits formed in insert 22 leading to passages formed by slots in the exterior of the insert in co-operation with the wall of the thermowell 17.

We claim:

1. A gas flow correction sensor for sensing a pressure-temperature function of gas flowing in a line for use in correcting the output of a volumetric flow meter connected in the line, the sensor comprising:
    a sealed gas-containing chamber having at least a portion thereof in a thermowell entering the line, said chamber including a bellows subjected to line pressure and said portion comprising a capillary tube connected with a sub-chamber, whereby the contained gas will be maintained at line temperature and pressure; and
    a vibrating element density sensing means for producing an output signal whose frequency is dependent upon the density of the contained gas, the density sensing means being mounted in said sub-chamber.

2. A sensor as claimed in claim 1, wherein the density sensing means comprises a resonant quartz density sensor.

3. A sensor as claimed in claim 1, further comprising a second density sensing means similar to the first mentioned sensing means but arranged to be subjected only to line temperature, for cancelling intrinsic temperature dependent errors of the first sensing means.

4. A sensor as claimed in claim 1, wherein the contained gas is chosen to be of comparable compressibility with the gas being metered.

5. A sensor as claimed in claim 1, wherein the capillary and sub-chamber are formed within an elongate probe in said thermowell.

6. A sensor as claimed in claim 1, wherein the bellows volume is large compared with the volume of any capillary and sub-chamber portions.

7. A sensor as claimed in claim 2, further comprising a second density sensing means similar to the first mentioned sensing means but arranged to be subjected only to line temperature, for cancelling intrinsic temperature dependent errors of the first sensing means.

* * * * *